United States Patent [19]

Clayman

[11] Patent Number: 5,628,746

[45] Date of Patent: May 13, 1997

[54] DILATATION CATHETER ASSEMBLY WITH CUTTING ELEMENT AND METHOD OF USING THE SAME

[75] Inventor: Ralph V. Clayman, St. Louis, Mo.

[73] Assignee: Applied Medical Resources Corporation, Laguna Hills, Calif.

[21] Appl. No.: 347,838

[22] Filed: Nov. 30, 1994

Related U.S. Application Data

[63] Continuation of Ser. No. 873,712, Apr. 22, 1992, abandoned, which is a continuation of Ser. No. 522,148, May 11, 1990, abandoned, which is a continuation-in-part of Ser. No. 298,477, Jan. 18, 1989, abandoned.

[51] Int. Cl.$^6$ .................................................. A61B 17/39
[52] U.S. Cl. .......................... 606/45; 606/159; 606/194; 606/192
[58] Field of Search ........................... 606/47, 113, 159, 606/192, 194, 45, 46, 48; 604/96

[56] References Cited

U.S. PATENT DOCUMENTS

| | | |
|---|---|---|
| 3,435,826 | 4/1969 | Fogarty . |
| 3,467,101 | 9/1969 | Fogarty et al. . |
| 3,791,387 | 2/1974 | Itoh . |
| 3,896,815 | 7/1975 | Fettel et al. . |
| 3,910,279 | 10/1975 | Okada et al. . |
| 3,911,927 | 10/1975 | Rich et al. . |

(List continued on next page.)

FOREIGN PATENT DOCUMENTS

| | | | |
|---|---|---|---|
| 0336903 | 4/1988 | European Pat. Off. . | |
| 0315730 | 5/1989 | European Pat. Off. . | |
| 2427540 | 12/1979 | France . | |
| 2594322 | 8/1987 | France . | |
| 2426781 | 12/1975 | Germany . | |
| 3402573 | 8/1985 | Germany . | |
| 3519626 | 12/1986 | Germany .............................. | 606/159 |
| 599802 | 11/1976 | U.S.S.R. . | |
| 938977 | 7/1982 | U.S.S.R. . | |
| 8901800 | 3/1989 | WIPO . | |

OTHER PUBLICATIONS

Banning G. Lary, MD, et al., "Myocardial Revascularization Experiments Using the Epicardium" *Archives of Surgery* vol. 98, pp.69–72, Jan. 1969.
Banning G. Lary, MD, "Coronary Artery Resection and Replacement by a Blood Conduit" *Surgery* vol. 65, No. 4, pp.584–589, Apr. 1969.
Banning G. Lary, MD, "An Epicardial Purse String Suture for Closing Coronary Arteriotomy" *The American Surgeon* vol. 33, No. 3, pp.213–214, Mar. 1967.
Banning G. Lary, MD et al., "A Method for Creating a Coronary Myocardial Artery" *Surgery* vol. 59, No. 6, pp.1061–1064, Jun. 1966.
Banning G. Lary, MD, "Method for Increasing the Diameter of Long Segments of the Coronary Artery" *The American Surgeon* vol. 32, No. 1, pp.33–35, Jan. 1966.
Banning G. Lary, MD, "Coronary Artery Incision and Dilation" *Archives of Surgery* vol. 115, pp. 1478–1480, Dec. 1980.
Banning G. Lary, MD et al., "Experimental Vein Angioplasty of th Circumflex Coronary Artery" *Journal of Surgical Research* 17, pp.210–214, 1974.
Banning G. Lary, MD, "A Method to Create and Correct Stenosis of a Coronary Artery" *Archives of Surgery* vol.93, pp.828–830, Nov. 1966.

Primary Examiner—Michael H. Thaler
Attorney, Agent, or Firm—Richard L. Myers

[57] ABSTRACT

A dilatation catheter assembly is set forth which permits dilatation and incision of tissue whereby trauma and damage to the tissue due to uncontrolled tearing is reduced or eliminated. The assembly comprises an elongated tubular body having a distal end that carries a dilatation bladder and cutting element carried on the exterior of the bladder and that moves radially in concert with the exterior of the bladder as the bladder is inflated and deflated. The bladder is not linearly extensible and is extensible only to a specified volume and/or the cutting element utilized is a radio frequency cutting element.

13 Claims, 3 Drawing Sheets

U.S. PATENT DOCUMENTS

| | | |
|---|---|---|
| 3,923,065 | 12/1975 | Nozick et al. . |
| 3,982,544 | 9/1976 | Dyck . |
| 3,982,554 | 9/1976 | Saito et al. . |
| 4,273,128 | 6/1981 | Lary . |
| 4,311,143 | 1/1982 | Komiya . |
| 4,325,374 | 4/1982 | Komiya . |
| 4,326,530 | 4/1982 | Fleury . |
| 4,338,942 | 7/1982 | Fogarty . |
| 4,484,579 | 11/1984 | Meno . |
| 4,503,569 | 3/1985 | Dotter . |
| 4,564,014 | 1/1986 | Fogarty et al. . |
| 4,660,560 | 4/1987 | Klein . |
| 4,669,469 | 6/1987 | Gifford . |
| 4,709,698 | 12/1987 | Johnston et al. ............... 604/114 X |
| 4,747,405 | 5/1988 | Leckrone ............... 606/7 X |
| 4,793,348 | 12/1988 | Palmaz ............... 606/1 X |
| 4,799,479 | 1/1989 | Spears . |
| 4,886,061 | 12/1989 | Fischell et al. ............... 606/159 |
| 4,919,133 | 4/1990 | Chiang . |
| 4,976,711 | 12/1990 | Parins et al. ............... 606/48 |
| 4,998,539 | 3/1991 | Delsanti ............... 606/194 |
| 5,053,044 | 10/1991 | Mueller et al. ............... 606/159 |
| 5,073,166 | 12/1991 | Parks et al. . |
| 5,080,660 | 1/1992 | Buelna . |
| 5,196,024 | 3/1993 | Barath . |

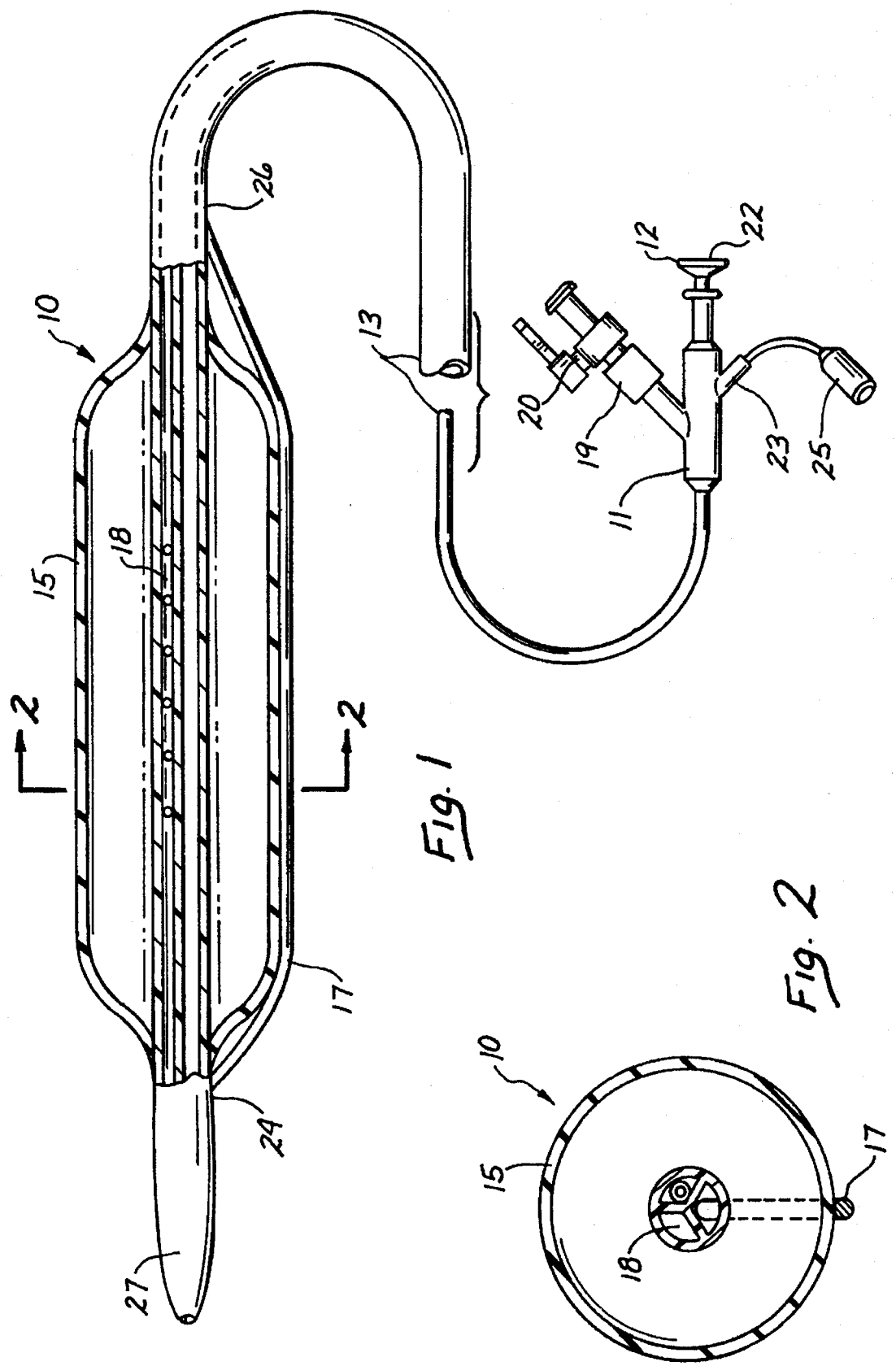

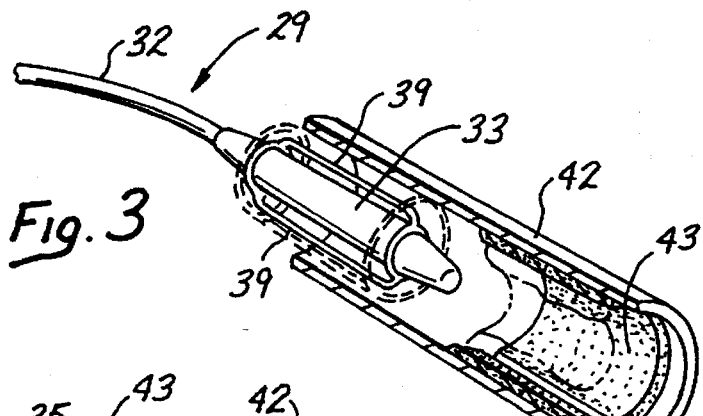
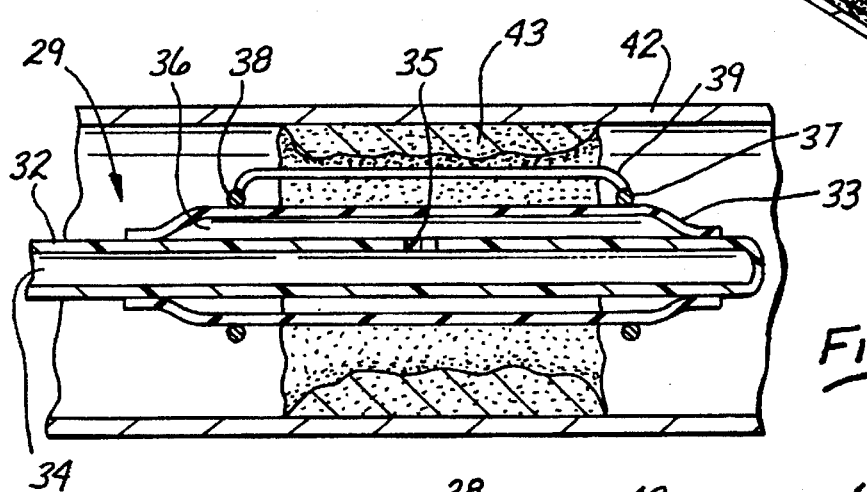
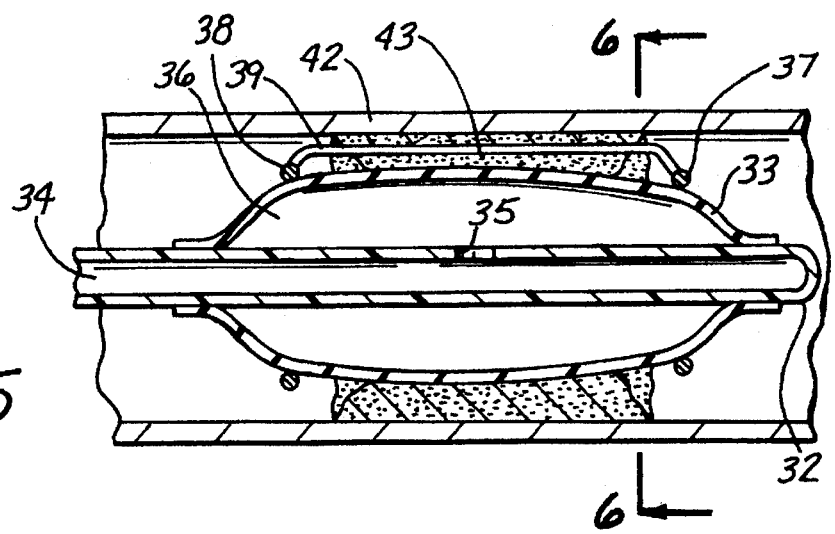
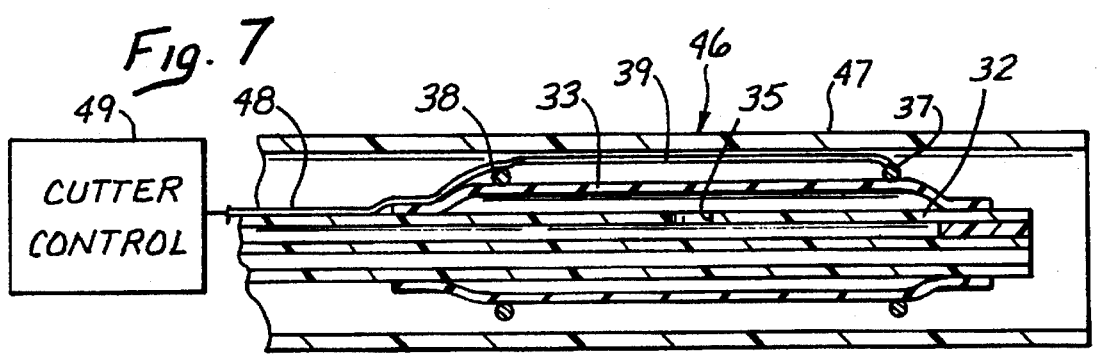

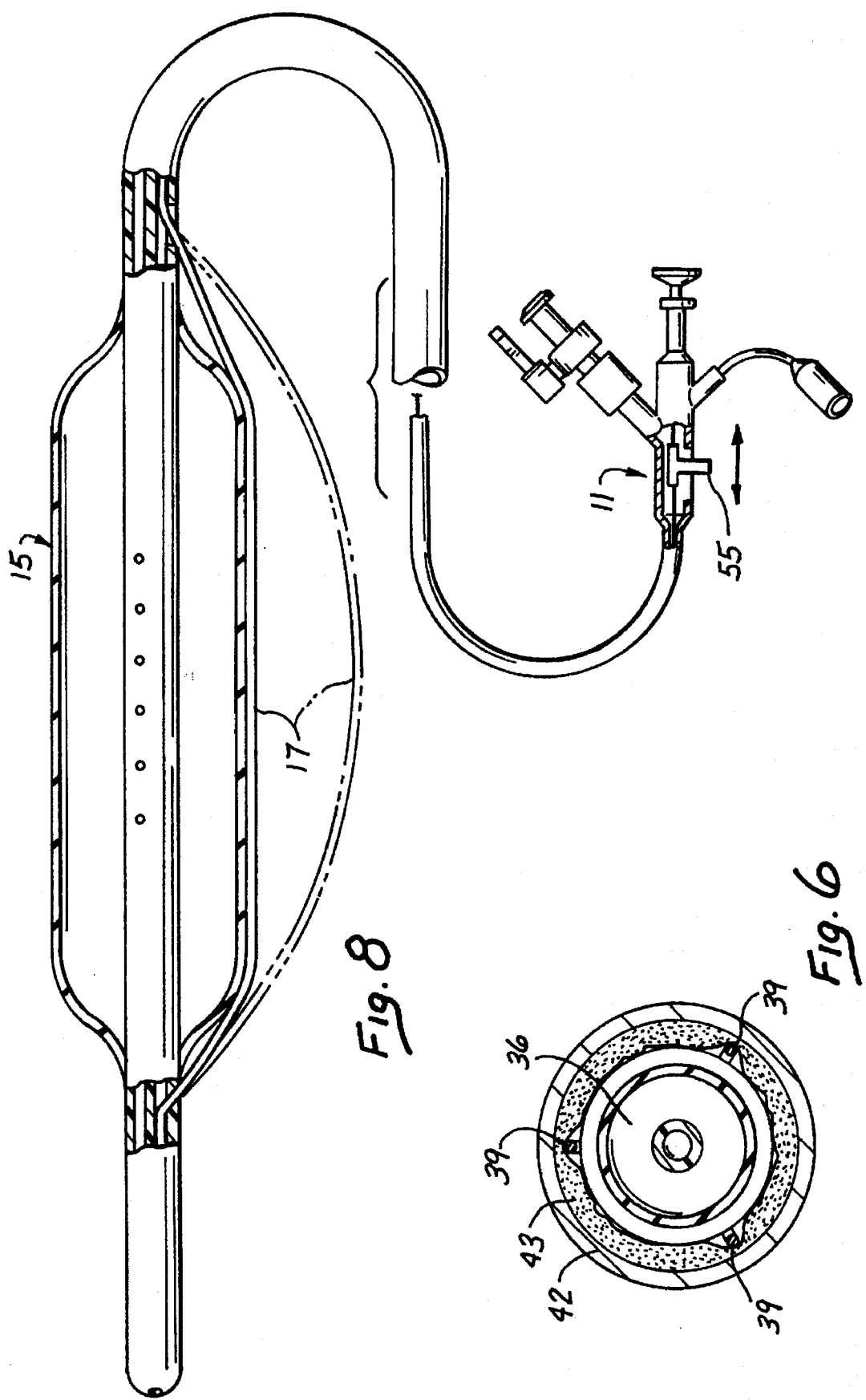

DILATATION CATHETER ASSEMBLY WITH CUTTING ELEMENT AND METHOD OF USING THE SAME

This is a continuation of application Ser. No. 07/873,712, filed Apr. 22, 1992, now abandoned which is a continuation of application Ser. No. 07/522,148, filed May 11, 1990, now abandoned which is a continuation-in-part of application Ser. No. 07/298,477, filed Jan. 18, 1989, now abandoned.

TECHNICAL FIELD

The present invention is in the field of surgical devices, particularly dilatation catheters. Specifically, it concerns a dilatation catheter whose expandable member carries a cutting element which concurrently incises the tissue being subjected to dilatation forces, thereby obtaining a clean and directed incision and reducing trauma and damage to such tissue from the dilatation forces.

BACKGROUND OF THE INVENTION

Dilatation catheters are used to dilate body vessels, orifices and conduits such as an artery narrowed by atherosclerotic plaque and/or fibromuscular disease or to dilate a constricted or obstructed ureter or urethra. The prior art devices basically consist of an elongated catheter having an inflatable extensible elastomeric (rubber-like) or non-extensible balloon or bladder, at or near its distal end. A guide wire or other axial support means is often included to improve the torque control or "steerability" of the apparatus.

The major advantage of dilatation catheter use over conventional surgery is that it is less invasive. Nonetheless, the tissue that is stressed is often also subjected to significant trauma. As the bladder expands, it exerts pressure on the surrounding tissue, causing the tissue to compress, deform and expand. The tissue, of course, has an inherent limit of deformability. When the dilation pressure causes the tissue to deform beyond that limit, the tissue tears apart, often to form a jagged wound, with considerable damage, trauma, pain and bleeding. A principal object of the present invention is to provide a dilatation catheter that permits tissue to be stressed, even beyond its limit of deformability, without experiencing uncontrolled tearing and the undesirable conditions associated therewith.

U.S. Pat. No. 4,747,405, issued to Leckrone on May 31, 1988, U.S. Pat. No. 4,669,469, issued Jun. 2, 1987 to Gifford, III, et al., and PCT/U.S. 86/02617 application of Leckrone, published Jun. 16, 1988 are each concerned with atherecotomy devices wherein a balloon is used to position an opening in a casing about an obstruction such as plaque. The balloon does not carry a cutting element to incise tissue but does carry means for disintegrating the plaque which is generally entrapped within a hole in the casing. The balloon basically positions the hole in the casing up against and about the plaque. Thus, the balloon is not symmetrically located within the blood vessel, an outward cutting element is not present and the blood vessel is not torn by the dilation force.

U.S. Pat. No. 4,799,479, issued Jan. 24, 1989 to Spears, shows use of a balloon to open up an artery and then utilizes a laser, heated wire mesh, or the like, to heat up blood trapped between the mesh and the plaque so that dilation will be maintained and so that a smooth wall will result.

U.S. Pat. No. 4,273,128, issued Jun. 16, 1981 to Lary, teaches the use of a balloon with a knife blade, or a series of knife blades, longitudinally distally removed from the balloon.

Soviet Patent 599802 published in 1976 utilizes a balloon which is located within a tube. When the balloon is extended this forces a cutting element through a window in the tube to accomplish fenestration. Pressure is not exerted on body tissue as the bladder is within the tube.

German Patent 3,402,573 is concerned with a single lumen multi-purpose catheter with an extensible elastic balloon with a cutting facility for treatment of stenosis. This patent utilizes three balloons of equal size at the distal end of the catheter. Each elastomeric balloon carries small cutter elements which extend in the longitudinal direction and which are held in a trough made of hard rubber or plastic. Prior to use the cutters lie hidden in longitudinal slots of the relatively thick wall of the one-lumen catheter. Threads anchor the plate when the balloons are inflated thereby limiting the degree of penetration of adjacent plaque (and possibly tissue).

U.S. Pat. No. 4,484,579, issued to Meno, et al, Nov. 27, 1984 is concerned with a commissurotomy catheter which serves for separating fused heart valve leaflets. The device includes four balloons carried by a single catheter structure. In use the device fits through the valve with two balloons on each side of the valve. A nylon or similar string is attached between the pairs of balloons on each side of the valve. The balloons can be alternately expanded and contracted thereby causing the strings strung between each pair of balloons to saw or pulsate into fused portions of the heart valve leaflets and separate them. The actual cutting portion of the string is not carried on the exterior of the balloons.

U.S. Pat. No. 4,660,560, issued Apr. 28, 1987 to L. A. Klien discloses an apparatus for relieving obstruction of the urinary tract caused by an enlarged prostate gland. A balloon is inserted via a urethral catheter and then is expanded until the prostate has been forced back from around the urethra. The apparatus of this patent does not employ a cutter of any sort.

The above-mentioned patents do not make use of a cauterizing (i.e. an electrosurgical or radio frequency surgical) cutting element. Nor do the above discussed patents either suggest or show any advantages for utilizing an inextensible bladder or balloon, i.e., a balloon which is not elastomeric (or elastic) and which can be inflated to only a selected shape and volume and which cannot extend longitudinally when pressurized. Furthermore, the above discussed patents are not concerned with a radially symmetrical, generally cylindrical in shape when expanded, balloon which extends longitudinally along a body passage and a cutting element which extends longitudinally along and generally parallel to the balloon, which balloon creates a substantially uniform tangential tension in tissue being cut, and which cutting element at the same time performs the necessary cutting whereby a clean longitudinally extending incision results and uncontrolled tearing of the tissue does not occur.

In radio frequency electrosurgical cutting a radio frequency current is allowed to pass from an active cutting electrode through a patient's tissue and into a grounding pad or cable. The current cuts tissue at the active cutting electrode, the cutting rate being dependant on current density through the tissue in that area. At low current density heat is generated but no cut is achieved. At high current density fast cutting occurs.

Current density depends on the voltage applied and can be controlled utilizing an adjustment present on a conventional generator utilized for this purpose. The current density also depends on the series impedance of the overall circuit. Series impedance is equivalent to the sum total of the resistance to the current throughout the circuit. It is affected by the material and the design of the active electrode, by the patient, by the type of tissue to be cut, and by the condition of contact established between the patient and the grounding pad as well as by the location of the pad relative to the cutting site. During surgery, the generator setting is usually adjusted to compensate for this variability and to reflect the surgeon's preference. Generators used in this type of surgery have a wide range of power output to accommodate a variety of procedures and devices. For example, the generator can be adjusted to cut tissue, or to cauterize adjacent already cut or torn tissue, or to do both.

The objective in electrosurgical cutting is to heat the tissues cells so rapidly that they explode into steam leaving a cavity in the cell matrix. The heat is meant to be dissipated in the steam and to not conduct through the tissue to thereby dry out adjacent cells. When the electrode is moved and fresh tissue is contacted new cells are exploded and the incision is made. Such electrosurgical cutting involves the sparking of the current to the tissue. The current utilized is in the radio frequency range and operates by the radio frequency current jumping across an air gap to the tissue. This is known as sparking.

An explanation of electrosurgical cutting theory can be found in the SSE3B Instruction Manual published by Valleylab of Boulder, Colo. on Apr. 1, 1979.

An advantage of electrosurgical cutting, particularly if it is performed utilizing a cutting electrode as disclosed in copending application Ser. No. 522,254, of Buelna, commonly assigned herewith, which is hereby incorporated herein in its entirety by reference, is that overheating of adjacent tissue with accompanying desiccation and damage is limited or prevented. Thus, what one can obtain is a clean cut without damage to adjacent tissue. A clean controlled cut is particularly desirable to assure that tearing does not occur in a direction away from the desired orientation of the cut.

The present invention is directed to overcoming one or more of the problems as set forth above.

Disclosure of Invention

In accordance with an embodiment of the invention a dilatation catheter assembly comprises in combination: an elongated tubular body having a distal end carrying a radially dilatable inextensible longitudinally extending member adapted to be positioned longitudinally along a body conduit and to dilate in a radially symmetrical manner and exert pressure on surrounding body tissue to provide a substantially uniform tangential tension therein; means for dilating the dilatable member to a constant inextensible volume and a cutting element carried on the exterior of the dilatable member that moves radially in concert with the exterior of the dilatable member and is adapted to incise said tissue, thereby reducing damage to said tissue from dilation forces.

In accordance with another embodiment of the invention a dilation catheter assembly comprises an elongated tubular body having a distal end carrying a radially dilatable member adapted to be positioned in body conduit and exert pressure on surrounding body tissue; means for dilating the dilatable member and an electrosurgical cutting element carried on the exterior of the dilatable member that moves radially in concert with the exterior of the dilatable member and that is adapted to incise the tissue, thereby reducing damage to the tissue from dilation forces.

In use the novel catheter of the invention concurrently exerts pressure on the tissue thereby placing it under tension and makes a clean, sharp generally longitudinally extending incision in the tissue while the tissue is subjected to the dilatation forces exerted by the dilating member. The incision allows the tissue to separate along a predetermined path and in a relatively clean, trauma-free manner as compared to the uncontrolled tearing that occurs when using prior devices.

Accordingly, another aspect of the invention is a method for dilating a body conduit, vessel or orifice comprising: inserting thereinto a dilatation catheter assembly comprising an elongated tubular body having a distal end carrying a radially dilatable inextensible member adapted to be positioned in a body conduit and to dilate in a radially symmetrical manner and exert pressure on surrounding body tissue to provide a substantially uniform tangential tension therein and a cutting element carried on the exterior of the dilatable member; dilating the inextensible dilatable member to an extent that causes the tissue to be stressed by the dilatable member; incising the stressed tissue using the cutting member; radially contracting the dilatable member to cause the dilatable member and cutting element to disengage the tissue; and withdrawing the dilation catheter assembly therefrom. The dilating and incising steps are suitably repeated until the dilatable member has reached a desired volume prior to the radial contracting step.

Still another aspect in accordance with the present invention is a method for dilating a body conduit, vessel or orifice. The method comprises inserting thereinto a dilation catheter assembly comprising an elongated tubular body having a distal end carrying a radially dilatable member adapted to dilate and exert pressure on surrounding body tissue and an electrosurgical cutting element carried on the exterior of the dilatable member; dilating the dilatable member to an extent that causes the tissue to be stressed by the dilatable member; activating the electrosurgical cutting element such that the stressed tissue is incised by the cutting element; discontinuing activation of the electrosurgical cutting element; radially contracting the dilatable member to cause the dilatable member and cutting element to disengage the tissue; and withdrawing the dilation catheter assembly therefrom. The dilating and incising steps are suitably repeated until the dilatable member has reached a desired volume prior to the radial contracting step.

BRIEF DESCRIPTION OF THE DRAWINGS

The invention will be better understood by reference to the figures of the drawings wherein like numbers denote like parts throughout and wherein:

FIG. 1 is a partly cross-sectional, isometric view of one embodiment of the invention catheter;

FIG. 2 is a cross-sectional view taken along line 2—2 of FIG. 1;

FIG. 3 is a prospective, schematic sectional view of a portion of another embodiment of the invention catheter positioned within a body conduit;

FIG. 4 is a sectional, side view of the embodiment of FIG. 3 in its deflated state;

FIG. 5 is a sectional side view of the embodiment of FIG. 3 in its inflated state;

FIG. 6 is a cross-sectional view along line 6—6 of FIG. 5;

FIG. 7 is a sectional elevational view of another embodiment of the invention; and FIG. 8 is a view similar to FIG. 1 and which includes means for selectively incising more deeply into a patient's tissue.

BEST MODE FOR CARRYING OUT INVENTION

FIG. 1 depicts a dilatation catheter assembly, generally designated 10, that may be used for dilating a body vessel or conduit, such as a ureter or urethra, to treat a blockage or other obstruction. The main elements of catheter assembly 10 are: an adapter 11 that defines the proximal end 12 of the assembly 10 and a site for various ports to the assembly 10; a triple lumen catheter body 13 (FIG. 2); an inflatable inextensible balloon or bladder member 15; and a cutting element 17, very preferably a radio frequency cutting element activatable by a radio frequency power source. The electrosurgical cutting element or electrode 17 is in the nature of a wire which runs along generally parallel to the longitudinally extending inflatable bladder 15. In use, the bladder 15 is inserted longitudinally into a body conduit to the position where a surgical cut is required. The bladder 15 is then inflated (an inextensible bladder is generally used) to a desired pressure about 1 atmosphere) and allowed to expand to occupy the space in the body vessel or conduit. Radio frequency current is then passed through the cutting element 17. This leads to the wire being moved outwardly and incising adjacent tissue in that direction. Thereafter, the pressurization and incising steps are suitably repeated (the pressure drops each time incising occurs) as many times as is necessary until the bladder 15 is fully inflated. In this way, the depth of the incision is controlled by the size chosen for the inextensible bladder 15 and tearing is avoided by making successive cuts rather than exerting a very large pressure within the bladder and overstressing the body conduit.

The material used for the wire can be any of the materials currently used for electrosurgical cutting wires. For example, the wire can be made of stainless steel or tungsten. In accordance with the teachings in the previously mentioned copending Buelna patent application a sheath with a slit in it, the slit facing away from the bladder 15, surrounds the cutting element 17. As seen in FIG. 2, one of the three lumens serves as an inflation/deflation passageway 18, a second serves as a drainage/infusion passageway, and a third carries cutting element 17.

In accordance with the present invention the inflatable balloon or bladder member 15 is of the inextensible or constant volume variety, that assumes, when expanded, a specific size and shape. Thus, the balloon member 15 cannot extend significantly longitudinally within a body conduit beyond its selected length. And, further, it can only extend radially to a selected radius, thus controlling the depth of the incision. Since the balloon member 15 cannot extend longitudinally, as can elastic or elastomeric balloons, it must exert the force caused by inflation of the balloon member 15 radially against an enclosing body conduit or the like. In contrast, if an elastic or elastomeric balloon is expanded within a body conduit which has one portion particularly narrowed and particularly resistant to expansion, the balloon will simply elongate rather than acting radially outwardly against the constriction. What is happening is a balance of forces in the balloon which then expands in the direction of least resistance.

In accordance with the present invention it is preferred to utilize a radio frequency cutting element 17 for a number of reasons. One reason is that a radio frequency cutting element 17 will not perform any cutting unless and until it is activated by passing a radio frequency current through it. As a result, accidental cuts cannot be made away from the area where cutting is desired. And, with proper control cutting can be very sharply defined leading to a clean incision without tearing. This radio frequency cutting or cauterizing technique can, thus, provide significant advantages over the use of prior art cutters in an apparatus of the nature disclosed herein.

In accordance with the present invention the balloon member 15 generally extends longitudinally along the body conduit and is generally symmetrically placed and expandable therein. In this manner, as the balloon member 15 is expanded, it exerts a substantially equal tangential tension upon the tissue defining the body conduit. This results in the incision by the cutting element 17, which would generally proceed parallel to the balloon member 15, being particularly clean. In essence, the incision when made in this manner proceeds longitudinally along the body cavity and will generally not go off at an angle as might be the case if the tangential tension in the body conduit was not substantially uniform.

In accordance with the most preferred embodiment of the present invention the cutting element 17 is a radio frequency cutting element and is parallel to the bladder member 15, the bladder member 15 extends longitudinally along the body conduit and is of an inextensible (non-elastic, non-elastomeric) nature and is symmetrically placed within the body cavity so that on expansion it exerts a substantially uniform tangential tension upon the tissue defining the body cavity. This allows all of the advantages of the present invention to be realized at one and the same time.

The adapter 11 serves as a site for a bladder inflation/deflation port 19 that is attached to a source of inflation medium (not shown) for inflating the bladder member 15 or a suction source (not shown) for deflating the bladder member 15. Port 19 has a valve 20 for regulating the inflation medium or suction, as the case may be. Port 19 connects into the proximal end of an inflation/deflation passageway 18 that extends from the port 19 to the bladder member 15. The adapter 11 also serves as a site for the drainage tube inlet/outlet port 22 and a cutting element port 23. The drainage port 22 is connected to the proximal end of the lumen that carries a stylet or guide wire. The drainage port 22 may serve as a site for removing fluid from the lumen or as a site for infusing fluid into the lumen. The distal end of the catheter body has a series of drain holes 24 to facilitate flushing the lumen with fluid or voiding the bladder member 15. A "banana plug" cutting element connector 25 is affixed to the end of the cutting element port and the cutting element 17 extends from the connector through the lumen of the catheter body 13 and exits therefrom via an aperture 26 and continues along the exterior of the bladder member 15. The cutting element 17 can consist of a thin wire which has an external incising edge that faces outwardly from the bladder member 15. Alternatively, the cutting element 17 may be a sharp edge, beam, or, more preferably, a radio frequency cutting or cauterizing element 17. The element/bladder is/are constructed (e.g., the element 17 is flexible or expandable) such that the cutting element 17 is carried on the exterior of the bladder member 15 (at least when the bladder member 15 is inflated) but is not capable of incising the bladder member 15. If desired, the portion of the exterior of the bladder member 15 that is exposed to the cutting element 17 may carry a protective cover (not shown) to further guard against the bladder member 15 being incised by the cutting element 17. The cutting element 17 may be carried at a predetermined spacing from the bladder surface or directly on the surface. When carried on the surface the cutting element 17 may be an integral part of the surface or attached to the surface. If desired the cutting element 17 may be extended/retracted manually via the connector into/out of the catheter body 13.

For use in urethral dilatation the distal end of the assembly 10 includes an atromatic tip 27. Such structure may not be necessary or desirable for dilating other conduits/orifices. For urethral dilation, the assembly 10 may optionally include another lumen and "Foley" type balloon (not shown) distally of the dilatation bladder member 15 to anchor the catheter in the bladder neck of the human body to facilitate correct positioning of the dilatation bladder member 15 and minimize the possibility of migration and displacement of the assembly 10.

One or more of the catheter assembly components may be made of radiopaque materials to facilitate the visualization of the assembly 10 by the physician during placement of the assembly 10 in the body vessel/conduit.

A typical surgical procedure in which the catheter assembly 10 is employed involves the following steps. A cytoscope is first inserted into the vessel/conduit/orifice to be dilated. Calibration devices may be inserted through the cytoscope to facilitate measuring the extent of the vessel/conduit/orifice being dilated. The dilatation catheter of FIG. 1 is then inserted to the desired depth in the vessel/conduit. A cytoscope lens may then be inserted to allow visualization of the catheter and the bladder location. Fluid may be infused through the drainage tube or cytoscope to facilitate such visualization. Once in position, the bladder member 15 is inflated. Such inflation causes the cutting element 17 to move radially outwardly as the bladder surface expands radially until the cutting element 17 contacts the surrounding tissue. In accordance with a preferred embodiment of the invention the bladder member 15 is inextensible as mentioned previously.

As used herein the term "tissue" is intended to include, without limitation, normal tissue, stomatic tissue, neoplastic tissue (tumors) or an obstruction such as plaque. Continued radial expansion of the bladder member 15 positions the cutting element 17 and causes the bladder member 15 to exert pressure on the tissue thereby subjecting the tissue to a substantially uniform tangential tension. If the preferred radio frequency cutting element 17 is utilized a radio frequency current is passed through it. This combined cutting and dilating action results in the tissue being expanded without being torn due to a buildup of excess stresses within the tissue. Instead, the tissue is cut in a clean, concentrated, generally longitudinal fashion by the cutting element 17 and the dilatation does not uncontrollably tear the tissue and cause excessive trauma and bleeding. The inflated bladder member 15 provides the additional benefit of acting as a tamponade to reduce bleeding. The radio frequency cutting element 17 is such that it incises the surrounding tissue in a manner such as to cause controlled incising under the combined cutting and dilating action.

After the vessel/conduit/orifice tissue is incised and dilated and the blockage/obstruction is relieved, the power through the radio frequency cutting element 17 is disconnected, if such a cutting element is used, the bladder member 15 is deflated by connecting the inflation/deflation port 19 to suction or atmospheric pressure and opening the inflation/deflation port valve 20 thereto. Deflation of the bladder member 15 results in a simultaneously radial retraction of the cutting element 17 out of contact with the tissue. Once the bladder member 15 is deflated the cutting element 17 may be retracted via the connector 25. If desired, the cutting element 17 may be retracted prior to complete deflation of the bladder member 15 and/or the bladder member 15 reinflated and left in place to act as a tamponade. Often it is desirable to leave the cutting element 17 in contact with the wound for a time, for example from about 10 minutes to about 2 hours, until the bleeding stops or is under control, and then to deflate the bladder member 15 and withdraw the catheter. Alternatively, the catheter can simply be withdrawn from the vessel/conduit altogether. The particular details of operation are determined by the surgeon depending upon the particular procedure being carried out and the particular person being operated upon.

FIGS. 3–6 depict another dilatation catheter assembly of the invention, generally designated 29, in use. Only the distal end of the assembly 29 is shown. Adapter(s), inflation/deflation ports are not shown for convenience. The distal end is defined by a closed end catheter tube 32 which carries an inflatable, preferably inextensible, bladder member 33 on its exterior. The lumen 34 of the tube 32 is connected to the source of inflation fluid/suction, as the case may be. The tube 32 has a radial aperture 35 that opens into the lumen 36 of the bladder member 33. A pair of expandable ring-shaped members 37,38 extend around the exterior of the bladder member 33 near the distal and proximal ends thereof. One or more cutting elements 39 are affixed between the rings so that they extend longitudinally and outwardly therefrom.

FIGS. 3 (in solid line) and 4 show the assembly 29 in its deflated state positioned within a vessel 42 partially obstructed by an obstruction 43. In order to inflate the bladder member 33, pressurized fluid is passed through catheter tube lumen 34 and aperture 35 into the bladder lumen. Inflation of the bladder member 33 in turn causes the ring members 37,38 to expand and move the cutting element (s) 39 radially outward. FIGS. 3 (phantom line), 5, and 6 show the bladder member 33 in an inflated state with the cutting element 39 incising the obstruction.

FIG. 7 shows yet another dilatation catheter assembly, generally designated 46, of the invention. The assembly 46 is shown in its deflated state. This assembly 46 is similar in structure to assembly 29 except that the assembly 46 is housed within a sheath or introducer 47 and a cauterizing element 48 is connected to the cutting element 39. The sheath permits the assembly 46 to be introduced into the vessel in an unexposed manner, ejected from the end thereof for use, and retracted back into the sheath 47 after use. The ejection and retraction may be achieved by relative longitudinal movement of the sheath 47, assembly 46, or both. The cutting element 39 can be a radio frequency cutting element and cauterization will result along with the cutting. Also, following cutting a coagulation producing radio frequency signal can be passed through cutting element 39.

FIG. 8 illustrates an embodiment of the invention wherein the cutting element 17 can be advanced beyond the supporting surface of the bladder 15. In the embodiment of FIG. 8 the cutting element 17 has an actuator 55 attached to it in the area of the adapter 11, the actuator extending through the adapter 11. After incision has been completed using the bladder 15, that is, after the bladder 15 has been fully extended and the cutting element 17 has cut as deeply as it will when supported by the bladder 15, the surgeon can electively advance the actuator 55, thereby advancing the cutting element 17 and causing it to bow outwardly and away from the bladder 15 and, when a radio frequency current is passed through it, incise further into the tissue a desired distance.

Industrial Applicability

The present invention provides an apparatus and method for controlled surgical dilation and incision within body conduits, vessels and orifices which virtually eliminates tearing and trauma caused by dilation beyond the strength of the tissue forming the body conduit, vessel or orifice being dilated.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A method for dilating a body conduit defined by body tissue, the method including the steps of:

providing a tubular body having an elongate axis extending between a distal end and a proximal end, a cutting element comprising not more than one cylindrical electrosurgical cutting wire being disposed in proximity to the distal end of the tubular body in a particular orientation with the axis;

inserting the tubular body with the cutting element into the body conduit;

advancing the cutting element generally radially outwardly of the tubular body to contact the body tissue of the conduit, the cutting element moving generally in a plane which includes the axis of the tubular body while it is advancing;

activating the cutting element in contact with the tissue to create in the tissue an incision defined by tissue walls; and creating in the surrounding tissue a tangential force acting to separate the tissue walls of the incision thereby expanding the body cavity.

2. The method recited in claim 1 wherein the tubular body includes an inflatable member disposed between the tubular body and the cutting element and during the advancing step the dilatable member is dilated to move the cutting element radially outwardly into contact with the surrounding tissue of the body conduit.

3. The method recited in claim 2 wherein during the creating step the dilatable member is dilated to contact the surrounding tissue and create in the surrounding tissue the dilation forces.

4. A dilation catheter assembly adapted for insertion into the urethra of a patient, comprising in combination:

an elongate tubular body having an axis and a distal end carrying a generally cylindrical radially dilatable member adapted to be positioned longitudinally in a body conduit and having properties for dilating generally radially of the tubular body;

means for dilating the dilatable member to exert dilation forces on the urethra;

cutting means carried by the tubular body exteriorly of the dilatable member, for creating an incision in the urethra thereby reducing damage to the urethra from the dilation forces; and the cutting means being limited to a single cutting element in the form of a thin cylindrical wire disposed longitudinally of the tubular body and movable radially in a plane including the axis of the tubular body to create the incision in the urethra, at least a portion of said wire being disposed radially outwardly of said tubular body at all times.

5. The assembly recited in claim 4 wherein the dilatable member is an inflatable bladder that is adapted to be connected to a source of inflation fluid.

6. The assembly recited in claim 5 wherein the cutting element is permanently affixed to the exterior surface of the inflatable bladder.

7. The assembly recited in claim 5 wherein the cutting element is adapted to be moved radially outwardly by the inflatable bladder.

8. The assembly recited in claim 4 wherein the cutting element is an integral component of the dilatable member.

9. A catheter for dilating a body conduit defined by living tissue, comprising:

a tubular body having an elongate axis extending between a distal end and a proximal end;

an elongate cutting element including only a single cylindrical wire disposed in proximity to the distal end of the tubular body and having properties for being moved along a plane including the axis between a retracted position in proximity to the tubular body and an extended position in proximity to the living tissue, the cutting element having characteristics for being activated to cut the living tissue when the cutting element is in the extended position;

means operable from the proximal end of the tubular body for moving the cutting element radially of the tubular body from the retracted position to the extended position in proximity to the living tissue; and means for activating the cutting element in the extended position to create an incision in the living tissue, the activating means including a generator having electrical power to create a current density in the tissue proximate to the cutting element in the extended position, the electrical power being sufficient to cut the tissue.

10. The catheter recited in claim 9 wherein the particular direction is generally radially of the tubular member.

11. The catheter recited in claim 9 wherein said single wire is disposed generally parallel to the axis of the tubular member and movable generally radially of the tubular member to cut the tissue.

12. The catheter recited in claim 9 wherein the body conduit is the urethra and the living tissue defining the urethra is the prostatic urethra.

13. The catheter recited in claim 9 wherein the body conduit is the ureter.

* * * * *